United States Patent [19]

Kelm et al.

[11] Patent Number: 5,189,066
[45] Date of Patent: Feb. 23, 1993

[54] PHARMACEUTICAL COMPOSITIONS OF TEBUFELONE

[75] Inventors: Gary R. Kelm, Cincinnati; Alan E. Bruns, Okeana, both of Ohio

[73] Assignee: The Procter & Gamble Company, Cincinnati, Ohio

[21] Appl. No.: 732,951

[22] Filed: Jul. 19, 1991

Related U.S. Application Data

[63] Continuation of Ser. No. 440,178, Nov. 22, 1989, abandoned.

[51] Int. Cl.$^5$ .............................................. A61K 31/12
[52] U.S. Cl. ..................... 514/678; 514/689; 514/960; 514/961; 514/941
[58] Field of Search ............... 514/678, 689, 960, 961, 514/941

[56] References Cited

U.S. PATENT DOCUMENTS

| | | | |
|---|---|---|---|
| 2,988,484 | 6/1961 | Barsky et al. | 424/107 |
| 3,867,521 | 2/1975 | Miskel et al. | 424/37 |
| 4,156,219 | 5/1979 | Sezaki | 424/118 |
| 4,325,942 | 4/1982 | Taki et al. | 424/94.1 |
| 4,690,816 | 9/1987 | Hata et al. | 424/456 |
| 4,690,823 | 9/1987 | Lohner et al. | 424/456 |
| 4,708,966 | 11/1987 | Loomans et al. | 514/689 |
| 4,786,495 | 11/1988 | Bird et al. | 424/81 |
| 4,797,288 | 1/1989 | Sharma et al. | 424/476 |
| 4,827,062 | 5/1989 | Saeki et al. | 514/690 |
| 4,847,303 | 7/1989 | Loomans et al. | 549/689 |
| 4,849,428 | 7/1989 | Dobson et al. | 549/307 |
| 4,853,379 | 8/1989 | Shroot et al. | 514/179 |

OTHER PUBLICATIONS

Griffin, W. C., "Classification of Surface-Active Agents by 'HLB'", Journal of the Society of Cosmetic Chemists, vol. 1, No. 5 (1949), pp. 311-326.
CTFA Cosmetic Ingredient Dictionary, Third Edition (1984), N. F. Estrin, P. A. Crosely and C. R. Haynes, Eds., The Cosmetic Toiletry and Fragrance Association, Inc., Washington, D.C., pp. 39–40, 211, 238 & 247.
The National Formulary, 17th Edition (1990), The United States Pharmacopeial Convention, Inc., Rockville, Md., p. 1966.

Primary Examiner—Frederick E. Waddell
Assistant Examiner—T. J. Criares
Attorney, Agent, or Firm—M. B. Graff, IV; J. D. Schaeffer; T. H. O'Flaherty

[57] ABSTRACT

The subject invention involves compositions, consisting essentially of the drug active 1-3,5-bis(1,1-dimethylethyl)-4-hydroxyphenyl-5-hexyn-1-one (tebufelone) at a concentration of at least about 15%, and the balance a pharmaceutically-acceptable vehicle. The vehicle is formulated such that the compositions are homogeneous liquids at 37° C. and provide good solubilization of the drug active.

22 Claims, No Drawings

PHARMACEUTICAL COMPOSITIONS OF TEBUFELONE

This is a continuation of application Ser. No. 440,178, filed on Nov. 22, 1989, now abandoned.

TECHNICAL FIELD

The subject invention is concerned with novel pharmaceutical compositions containing tebufelone, a di-tert-butylphenol anti-inflammatory compound. More particularly, it is concerned with such compositions dosed per orally which provide good bioavailability of the compound.

BACKGROUND OF THE INVENTION

Certain substituted di-tert-butylphenol derivatives are known to be effective as anti-inflammatory, analgesic and/or antipyretic agents. Of particular interest regarding the subject invention is tebufelone, 1-3,5-bis(1,1-dimethylethyl)-4-hydroxyphenyl-5-hexyn-1-one, disclosed in U.S. Pat. No. 4,708,966 issued to Loomans, Matthews and Miller on Nov. 24, 1987. (The compound is termed 4-(5'-hexynoyl)-2,6-di-tert-butylphenol therein.) Related compounds are disclosed in U.S. Pat. No. 4,847,303 issued to Loomans, Matthews and Miller on Jul. 11, 1989 and U.S. Pat. No. 4,849,428 issued to Dobson, Loomans, Matthews and Miller on Jul. 18, 1989.

It is an object of the subject invention to provide pharmaceutical compositions for peroral administration of the above anti-inflammatory compound which provide good bioavailability of the compound.

SUMMARY OF THE INVENTION

The subject invention relates to compositions consisting essentially of the drug active 1-3,5-bis(1,1-dimethylethyl)-4-hydroxyphenyl-5-hexyn-1-one at a concentration of at least about 15%, and the balance a pharmaceutically-acceptable vehicle. The compositions have the properties of (1) being a homogeneous liquid at 37° C., (2) providing solubilization of the drug active at a level of at least 1 mg/mL in 0.1N HCl at 20° C., and (3) providing solubilization of the drug active in simulated intestinal fluid in 5 minutes or less.

DETAILED DESCRIPTION OF THE INVENTION

The drug active of interest regarding the subject invention is 1-3,5-bis(1,1-dimethylethyl)-4-hydroxyphenyl-5-hexyn-1-one having the chemical structure:

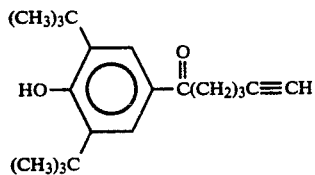

which is referred to herein as tebufelone. A method of synthesizing tebufelone is disclosed in aforementioned U.S. Pat. No. 4,708,966, which is hereby incorporated herein by reference.

The subject invention involves pharmaceutical compositions of tebufelone intended for peroral administration to humans and lower animals. It has been found that tebufelone is essentially water-insoluble (solubility less than 1 μg/mL) and very lipophilic. The therapeutic dose of tebufelone is approximately 100 mg per day in humans. It has been found that the absorption of tebufelone from the gastrointestinal tract is quite low when the drug active is dosed in conventional solid dosage forms, such as tablets or powders in capsules.

It has been found that good absorption of tebufelone from the gastrointestinal tract occurs only when the drug active is perorally administered in pharmaceutical compositions which provide both rapid solubilization of the drug active and also essentially complete solubilization of the drug active in the gastrointestinal fluids. As used herein, being solubilized means that the drug active exists in an aqueous medium in a form that is freely diffusible. A freely diffusible form is one that is capable of transversing the unstirred boundary layer present along the absorbing membrane of the gastrointestinal tract. Such freely diffusible forms include a pure aqueous solution of the drug active, an aqueous micellar solution of the drug active (drug molecules dissolved in surfactant micelles), and/or an emulsion of the drug active (liquid droplets containing drug active surrounded by a surfactant layer dispersed in an aqueous medium).

A composition of the subject invention consists essentially of tebufelone at a concentration of at least about 15%, and the balance a pharmaceutically-acceptable vehicle, the composition having the following properties:

(1) being a homogeneous liquid at 37° C.,
(2) providing solubilization of tebufelone at a level of at least 1 mg/mL in 0.1N HCl at 20° C., and
(3) providing solubilization of 20 mg of tebufelone in 500 mL of simulated intestinal fluid in 5 minutes or less.

As used herein, solubilization of a dispersion is considered to have occurred if substantially all of the dispersion will pass through a 0.45 μm filter. Whether the extent of solubilization of tebufelone meets requirement (2) above is determined by adding an amount of a composition containing 10 mg tebufelone to 10 mL 0.1N HCl, shaking to disperse the composition, and determining whether substantially all of the dispersion will pass through a 0.45 μm filter.

The rate of solubilization of tebufelone of requirement (3) above is determined using the USP dissolution testing Apparatus 2 (see *The United States Pharmacopia*, XXth Revision (1979), p. 959). An amount of a composition containing 20 mg tebufelone is added to 500 mL simulated intestinal fluid, USP (without pancreatin), containing 2% of a 50/50 mixture of sodium cholate and sodium deoxycholate. Whether sufficient solubilization has occurred is determined after 5 minutes of stirring by determining whether substantially all of the dispersion passes through a 0.45 μm filter. An aliquot of the dispersion which has been filtered through a 0.45 μm filter is assayed for tebufelone by ultraviolet spectrophotometric assay.

One aspect of the subject invention involves compositions having a vehicle comprising a surfactant or mixture of surfactants, the vehicle having the following properties:

(a) being a homogeneous liquid at 37° C.,
(b) having an HLB of from about 9 to about 13, and
(c) forming a stable dispersion in water at 20° C. at concentrations of 10% or less.

Preferred vehicles also have the following properties:

(d) being soluble in isopropanol at 20° C. at concentrations of 10% or less, and
(e) being soluble in cottonseed oil at 20° C. at concentrations of 1% or less.

As used herein, HLB refers to the hydrophilic/lipophilic balance of the molecule as described in Griffin, W. C., "Classification of Surface-Active Agents by 'HLB'", *Journal of the Society of Cosmetic Chemistry*, Vol. 1, No. 5 (1949), p. 311. The HLB of the vehicle is preferably from 10 to 12.

Compositions of the subject invention comprise at least about 15% tebufelone, preferably from about 15% to about 30% tebufelone, more preferably from about 18% to about 25% tebufelone, especially from about 18% to about 20% tebufelone.

Preferred examples of surfactants which can be used in compositions of the subject invention include the following: polysorbate 80* and polysorbate 81* available from ICI Americas, Inc., Wilmington, Del.; PEG-25 glyceryl trioleate* available from Goldschmidt Chemical Corp., Hopewell, Va.; poloxamer 182*, poloxamer 183* and poloxamer 184* available from BASF Corp., Parsippany, N.J.; and polyoxyl 35 castor oil** available from BASF Corp.; and mixtures thereof. (*See *CTFA Cosmetic Ingredient Dictionary*, Third Edition (1984), N. F. Estrin, P. A. Crosely and C. R. Haynes, Editors, The Cosmetic, Toiletry and Fragrance Association, Inc., Washington, D.C. **See *The National Formulary*, 17th Edition (1990), The United States Pharmacopeial Convention, Inc., Rockville, Md.)

Examples of surfactants which are preferably used as the sole surfactant in compositions of the subject invention include polysorbate 81, PEG-25 glyceryl trioleate, poloxamer 183 and poloxamer 184. Examples of surfactants which are preferably used as surfactant mixtures in compositions of the subject invention include the following: from about 25% to about 75% polyoxyl 35 castor oil and from about 75% to about 25% poloxamer 182, especially about 50% polyoxyl 35 castor oil and about 50% poloxamer 182; from about 10% to about 25% polysorbate 80 and from about 75% to about 90% poloxamer 182, especially about 17% polysorbate 80 and about 83% poloxamer 182.

The vehicle of the compositions of the subject invention may also comprise a lipophilic solvent for tebufelone. Preferred lipophilic solvents are triglycerides or mixtures of triglycerides having straight fatty chains which are saturated or unsaturated with from about 6 to about 10 carbon atoms. Other preferred lipophilic solvents are fatty acids or mixtures of fatty acids having saturated straight chains of from about 6 to about 10 carbon atoms, or unsaturated straight chains of from about 12 to about 18 carbon atoms. Preferred lipophilic solvents useful in compositions of the subject invention include caprylic/capric triglyceride* (Captex 300 ®), available from Capitol City Products Co., Columbus, Ohio; oleic acid; and linoleic acid.

Preferred compositions of the subject invention which have vehicles which are mixtures of lipophilic solvents and surfactants have vehicles comprising, preferably consisting essentially of, from about 25% to about 85% of the lipophilic solvent, and from about 15% to about 75% of the surfactant; more preferably from about 40% to about 70% of the lipophilic solvent, and from about 30% to about 60% of the surfactant.

Preferred examples of vehicles which are mixtures of lipophilic solvents and surfactants include the following: from about 20% to about 50% polysorbate 81 and from about 50% to about 80% caprylic/capric triglyceride, especially about 33% polysorbate 81 and about 67% caprylic/capric triglyceride; from about 2% to about 10% polyoxyl 35 castor oil, from about 15% to about 40% poloxamer 182, and from about 50% to about 83% caprylic/capric triglyceride, especially about 6% polyoxyl 35 castor oil, about 28% poloxamer 182 and about 66% caprylic/capric triglyceride; from about 10% to about 25% poloxamer 182, from about 10% to about 25% polyoxyl 35 castor oil, and from about 50% to about 80% oleic acid, especially about 17% poloxamer 182, about 17% polyoxyl 35 castor oil and about 66% oleic acid.

Especially preferred compositions of the subject invention consist essentially of the following combinations of components:

(a) from about 15% to about 20% tebufelone, from about 35% to about 45% polyoxyl 35 castor oil, and from about 35% to about 45% poloxamer 182;

(b) from about 15% to about 20% tebufelone, from about 12% to about 16% polysorbate 80, and from about 64% to about 73% poloxamer 182;

(c) from about 15% to about 20% tebufelone, from about 25% to about 30% polysorbate 81, and from about 50% to about 60% caprylic/capric triglyceride;

(d) from about 15% to about 20% tebufelone, from about 4% to about 6% polyoxyl 35 castor oil, from about 20% to about 25% poloxamer 182, and from about 50% to about 60% caprylic/capric triglyceride;

(e) from about 15% to about 20% tebufelone, from about 12% to about 16% poloxamer 182, from about 12% to about 16% polyoxyl 35 castor oil, and from about 50% to about 60% oleic acid.

Another aspect of the subject invention involves compositions having a vehicle comprising triglycerides interesterified with polyethylene glycol. These materials are liquid at 37° C. and have an HLB in the range of from about 3 to about 7, preferably from 5 to 7.

Preferred examples of such materials are glycolysed ethoxylated glycerides obtained by partial alcoholysis of natural vegetable oils, e.g., those available under the trade name Labrafil ® from Gattefosse Corp., Elmsford, N.Y. A preferred example of such material is Labrafil 2609 ®, glycolysed ethoxylated glycerides obtained by partial alcoholysis of corn oil with polyethylene glycol 400.

Preferred compositions of the subject invention consist essentially of tebufelone, preferably in the amounts listed above, and the balance a glycolysed ethoxylated glyceride. Especially preferred are compositions consisting essentially of from about 15% to about 20% tebufelone and from about 80% to about 85% glycolysed ethoxylated glyceride.

EXAMPLES

The following are non-limiting examples of compositions of the subject invention. The compositions are each made as follows:

(1) if a surfactant or lipid solvent component is a solid at room temperature, it is heated to melting;

(2) all components are mixed thoroughly until the tebufelone is dissolved in the composition.

EXAMPLE 1

| Component | Wt. % |
| --- | --- |
| Polyoxyl 35 Caster Oil | 41.0 |
| Poloxamer 182 | 41.0 |
| Tebufelone | 18.0 |

EXAMPLE 2

| Component | Wt. % |
| --- | --- |
| Polyoxyl 35 Caster Oil | 13.7 |
| Poloxamer 182 | 13.7 |
| Oleic Acid | 54.6 |
| Tebufelone | 18.0 |

EXAMPLE 3

| Component | Wt. % |
| --- | --- |
| Polysorbate 80 | 13.7 |
| Poloxamer 182 | 68.3 |
| Tebufelone | 18.0 |

EXAMPLE 4

| Component | Wt. % |
| --- | --- |
| Polysorbate 80 | 4.6 |
| Poloxamer 182 | 22.8 |
| Captex 300 | 54.6 |
| Tebufelone | 18.0 |

EXAMPLE 5

| Component | Wt. % |
| --- | --- |
| Polyoxyl 35 Castor Oil | 4.6 |
| Poloxamer 182 | 22.8 |
| Captex 300 | 54.6 |
| Tebufelone | 18.0 |

EXAMPLE 6

| Component | Wt. % |
| --- | --- |
| Labrafil 2609 | 82.0 |
| Tebufelone | 18.0 |

EXAMPLE 7

| Component | Wt. % |
| --- | --- |
| Polysorbate 81 | 27.4 |
| Captex 300 | 54.6 |
| Tebufelone | 18.0 |

Another aspect of the subject invention is unit dosage forms of compositions of the subject invention disclosed hereinabove. Compositions which are solid at room temperature can be reduced to a particulate form by conventional means such as by grinding, cutting or chopping, or by cooling a spray of liquid composition to form solid particles. Such particulate solids can be filled into hard gelatin capsule shells by conventional means. In addition, such compositions may be filled as hot liquids into hard gelatin capsule shells followed by cooling to allow the contents to solidify.

Preferred unit dosage forms of the subject invention are soft gelatin capsules or sealed hard gelatin capsules containing liquid or solidified compositions of the subject invention as disclosed hereinabove. The soft gelatin capsules are made by conventional means by filling liquid compositions of the subject invention into soft gelatin capsule shells. This can be done with the composition at room temperature if it is a liquid thereat, or by heating the composition above its melting temperature to produce a liquid, and filling such liquid into soft gelatin capsule shells. In a similar manner, sealed hard gelatin capsules containing liquid or solidified compositions of the subject invention can be made by conventional means.

While particular embodiments of the subject invention have been described, it will be obvious to those skilled in the art that various changes and modifications of the subject invention can be made without departing from the spirit and the scope of the invention. It is intended to cover, in the appended claims, all such modifications that are within the scope of this invention.

What is claimed is:

1. A composition consisting essentially of 1-3,5-bis(1,1-dimethylethyl)-4-hydroxyphenyl-5-hexyn-1-one as a drug active at a concentration of at least about 15% of the composition, and the balance a pharmaceutically-acceptable vehicle, the composition having the following properties:
   (1) being a homogeneous liquid at 37° C.,
   (2) providing solubilization of the drug active at a level of at least 1 mg/mL in 0.1N HCl at 20° C., and
   (3) providing solubilization of 20 mg of the drug active in 500 mL of simulated intestinal fluid in 5 minutes;

the vehicle comprising a surfactant or mixture of surfactants, the vehicle having the following properties:
   (a) being a homogeneous liquid at 37° C.,
   (b) having an HLB of from about 9 to about 13,
   (c) forming a stable dispersion in water at 20° C. at concentrations of 10%;

whereby the absorption of the drug active from the gastrointestinal tract is substantially greater for the composition when perorally administered than for conventional solid dosage forms of the drug active.

2. The composition of claim 1 wherein the vehicle additionally has the following properties:
   (d) being soluble in isopropanol at 20° C. at concentrations of 10%, and
   (e) being soluble in cottonseed oil at 20° C. at concentrations of 1%.

3. The composition of claim 1 wherein the surfactant is selected from the group consisting of polysorbate 81, poloxamer 182, poloxamer 183, poloxamer 184, PEG-25 glyceryl trioleate, and polyoxyl 35 castor oil, and mixtures thereof.

4. The composition of any of claims 1, 2 or 3 wherein the vehicle consists essentially of the surfactant or surfactant mixture.

5. The composition of claim 1 wherein the vehicle also comprises a lipophilic solvent selected from the group consisting of a triglyceride or a mixture of triglycerides having fatty chains of from about 6 to about 10 carbon atoms, straight-chain saturated fatty acids having from about 6 to about 10 carbon atoms, and straight-chain unsaturated fatty acids having from about 12 to about 18 carbon atoms, and mixtures thereof.

6. The compositions of claim 5 wherein the surfactant is selected from the group consisting of polysorbate 80, polysorbate 81, poloxamer 182, poloxamer 183, poloxamer 184, PEG-25 glyceryl trioleate and polyoxyl 35 castor oil, and mixtures thereof.

7. The composition of claim 6 wherein the vehicle consists essentially of from about 25% to about 85% of a lipophilic solvent which is selected from the group consisting of caprylic/capric triglyceride, oleic acid and linoleic acid; and from about 15% to about 75% of the surfactant.

8. The composition of claim 3 consisting essentially of from about 15% to about 20% tebufelone, from about 35% to about 45% polyoxyl 35 castor oil, and from about 35% to about 45% poloxamer 182.

9. The composition of claim 5 consisting essentially of from about 15% to about 20% tebufelone, from about 4% to about 6% polyoxyl 35 castor oil, from about 20% to about 25% poloxamer 182, and from about 50% to about 60% caprylic/capric triglyceride.

10. A composition consisting essentially of 1-3,5-bis(1,1-dimethylethyl)-4-hydroxyphenyl-5-hexyn-1-one as a drug active at a concentration of at least about 15% of the composition, and the balance a pharmaceutically-acceptable vehicle, the composition having the following properties:
   (1) being a homogeneous liquid at 37° C.,
   (2) providing solubilization of the drug active of at least 1 mg/mL in 0.1N HCl at 20° C., and
   (3) providing solubilization of 20 mg of the drug active in 500 mL of simulated intestinal fluid in 5 minutes;
the vehicle comprising triglycerides interesterified with polyethylene glycol, such that its HLB is from about 3 to about 7; whereby the absorption of the drug active from the gastrointestinal tract is substantially greater for the composition when perorally administered than for conventional solid dosage forms of the drug active.

11. The composition of claim 10 wherein the triglycerides interesterified with polyethylene glycol are glycolysed ethoxylated glycerides obtained by partial hydrolysis of natural vegetable oils.

12. The composition of claim 11 wherein the triglycerides interesterified with polyethylene glycol are glycolysed ethoxylated glycerides obtained by partial hydrolysis of corn oil with polyethylene glycol 400.

13. The composition of any of claims 10, 11 or 12 wherein the vehicle consists essentially of the triglycerides interesterified with polyethylene glycol.

14. A pharmaceutical unit dosage form comprising a composition of any of claims 3, 6, 8, 9 or 12 in a soft gelatin capsule shell.

15. A pharmaceutical unit dosage form comprising a composition of any of claims 3, 6, 8, 9 or 12 in a sealed hard gelatin capsule shell.

16. The composition of claim 1 wherein the surfactant is 100% polysorbate 81.

17. The composition of claim 1 wherein the surfactant is 100% PEG-25 glyceryl trioleate.

18. The composition of claim 1 wherein the surfactant is 100% poloxamer 183.

19. The composition of claim 1 wherein the surfactant is 100% poloxamer 184.

20. The composition of claim 1 wherein the surfactant is from about 25% to about 75% poloxyl 35 castor oil and from about 25% to about 75% poloxamer 182.

21. The composition of claim 1 wherein the surfactant is from about 10% to about 25% polysorbate 80 and from about 75% to about 90% poloxamer 182.

22. A method for obtaining good absorption of the drug active from the gastrointestinal tract by perorally administering the composition of any of claims 1, 3, 6, 10 or 11.

* * * * *